(12) United States Patent
Boyke et al.

(10) Patent No.: US 9,743,750 B2
(45) Date of Patent: Aug. 29, 2017

(54) ORAL CARE SYSTEM

(71) Applicant: COLGATE-PALMOLIVE COMPANY, New York, NY (US)

(72) Inventors: Christine Boyke, Somerset, NJ (US); Donghui Wu, Bridgewater, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 240 days.

(21) Appl. No.: 14/434,365

(22) PCT Filed: Oct. 18, 2012

(86) PCT No.: PCT/US2012/060776
§ 371 (c)(1),
(2) Date: Apr. 8, 2015

(87) PCT Pub. No.: WO2014/062186
PCT Pub. Date: Apr. 24, 2014

(65) Prior Publication Data
US 2015/0257522 A1    Sep. 17, 2015

(51) Int. Cl.
*A45D 24/22* (2006.01)
*A46B 15/00* (2006.01)
(Continued)

(52) U.S. Cl.
CPC .......... *A46B 15/0055* (2013.01); *A46B 11/00* (2013.01); *A46B 11/001* (2013.01); *A61C 19/066* (2013.01); *A46B 2200/1066* (2013.01)

(58) Field of Classification Search
CPC ... A46B 15/0055; A46B 11/00; A46B 11/001; A46B 11/0065; A46B 19/066; A46B 2200/1066
(Continued)

(56) References Cited

U.S. PATENT DOCUMENTS 2,399,660 A    5/1946  Boulicault
2,438,641 A    3/1948  Loehr
(Continued)

FOREIGN PATENT DOCUMENTS

CN    102711554    10/2012
EP    0 308 549     3/1989
(Continued)

OTHER PUBLICATIONS

International Search Report and the Written Opinion of the International Searching Authority issued in International Patent Application PCT/US2012/060776 mailed Sep. 19, 2013.
(Continued)

*Primary Examiner* — Rachel Steitz

(57) ABSTRACT

An oral care system including a toothbrush body having a cavity and a dispenser positioned within the cavity. In one aspect, the invention can be an oral care system comprising: a toothbrush body comprising a handle and a head, the toothbrush body extending along a longitudinal axis from a proximal end to a distal end; a plurality of tooth cleaning elements extending from the head; an opening in the proximal end of the toothbrush body that forms a passageway into an internal cavity of the handle; a first dispenser positioned within the internal cavity and comprising a first store of oral care material, the first dispenser resiliently coupled to the toothbrush body to be alterable between: (1) a first retracted state; and (2) a first extended state.

13 Claims, 3 Drawing Sheets

(51) Int. Cl.
*A46B 11/00* (2006.01)
*A61C 19/06* (2006.01)

(58) Field of Classification Search
USPC .......................................................... 132/311
See application file for complete search history.

(56) References Cited

U.S. PATENT DOCUMENTS

| | | | |
|---|---|---|---|
| 2,845,645 A | | 8/1958 | Wishnefsky et al. |
| 2,968,827 A | | 1/1961 | Lawsine |
| 3,359,991 A | | 12/1967 | Spatz |
| 3,734,118 A | | 5/1973 | Howard |
| 3,741,667 A | | 6/1973 | Cesari |
| 4,056,110 A | | 11/1977 | Landsman |
| 4,228,925 A | | 10/1980 | Mendelovich |
| 4,275,750 A | | 6/1981 | Clark |
| 4,296,518 A | | 10/1981 | Furrier et al. |
| 4,543,679 A | | 10/1985 | Rosofsky et al. |
| 4,576,190 A | | 3/1986 | Youssef |
| 4,759,381 A | | 7/1988 | Cesari |
| 4,865,481 A | | 9/1989 | Scales |
| 4,866,809 A | | 9/1989 | Pelletier |
| 4,879,781 A | | 11/1989 | Desimone |
| 5,010,906 A | | 4/1991 | Preciutti |
| 5,028,158 A | | 7/1991 | Fey |
| 5,244,298 A | | 9/1993 | Greenhouse |
| 5,301,808 A | * | 4/1994 | Pierson .................. A45D 40/24 132/297 |
| 5,339,483 A | | 8/1994 | Byun |
| 5,382,107 A | | 1/1995 | Nian |
| 5,403,105 A | | 4/1995 | Jameson |
| 5,415,187 A | | 5/1995 | Heneveld |
| 5,425,591 A | | 6/1995 | Contreras et al. |
| 5,476,334 A | | 12/1995 | Tello-Vallarino |
| 5,608,940 A | | 3/1997 | Panyon, Jr. |
| 5,611,687 A | | 3/1997 | Wagner |
| 5,862,817 A | | 1/1999 | Lee |
| 5,911,532 A | | 6/1999 | Evancic |
| 5,970,990 A | | 10/1999 | Dunton et al. |
| 5,980,145 A | | 11/1999 | Griffith |
| 6,056,469 A | | 5/2000 | Algorri |
| 6,099,315 A | | 8/2000 | Markowitz |
| 6,220,773 B1 | | 4/2001 | Wiegner et al. |
| 6,227,209 B1 | | 5/2001 | Kim et al. |
| 6,234,181 B1 | | 5/2001 | Lou |
| 6,290,417 B1 | | 9/2001 | Kaminski |
| 6,325,076 B1 | | 12/2001 | Ramirez |
| 6,439,885 B2 | | 8/2002 | Antler |
| 6,648,641 B1 | | 11/2003 | Viltro et al. |
| 6,672,783 B1 | | 1/2004 | Licata et al. |
| 6,895,976 B2 | | 5/2005 | Hetzler et al. |
| 7,143,462 B2 | | 12/2006 | Hohlbein |
| 7,237,974 B2 | | 7/2007 | Pfenniger |
| 7,264,471 B2 | | 9/2007 | Malcmacher et al. |
| 7,563,046 B2 | | 7/2009 | Patel |
| 7,677,827 B1 | | 3/2010 | Manukian |
| 8,052,016 B2 | | 11/2011 | Wang |
| 8,800,573 B2 | | 8/2014 | Hofstad |
| 2001/0045369 A1 | | 11/2001 | Pearlman et al. |
| 2002/0073496 A1 | | 6/2002 | Kim |
| 2003/0012594 A1 | | 1/2003 | Andersen |
| 2004/0020508 A1 | | 2/2004 | Earl |
| 2006/0067783 A1 | | 3/2006 | Tsaur |
| 2006/0260635 A1 | | 11/2006 | Dabney |
| 2006/0269351 A1 | | 11/2006 | McAfee |
| 2008/0118300 A1 | | 5/2008 | Burrowes |
| 2009/0288262 A1 | | 11/2009 | Hall |
| 2010/0067969 A1 | * | 3/2010 | Kang .................. A46B 11/0006 401/118 |
| 2010/0284726 A1 | | 11/2010 | Ottaviani et al. |
| 2011/0308030 A1 | | 12/2011 | Jimenez et al. |
| 2011/0314623 A1 | | 12/2011 | Jimenez et al. |
| 2012/0257920 A1 | | 10/2012 | Jimenez et al. |

FOREIGN PATENT DOCUMENTS

| | | |
|---|---|---|
| EP | 0 385 815 | 9/1990 |
| FR | 2752150 | 2/1998 |
| GB | 792448 | 3/1958 |
| GB | 1190280 | 4/1970 |
| GB | 2307674 | 6/1997 |
| GB | 2393642 | 4/2004 |
| JP | H9255021 | 9/1997 |
| JP | 2004344264 | 12/2004 |
| TW | M346326 | 12/2008 |
| WO | WO 83/03742 | 11/1983 |
| WO | WO 2005/065373 | 7/2005 |
| WO | WO 2010/132590 | 11/2010 |

OTHER PUBLICATIONS

Written Opinion of the International Preliminary Examining Authority issued in International Patent Application PCT/US2012/060776 mailed Oct. 20, 2014.

* cited by examiner

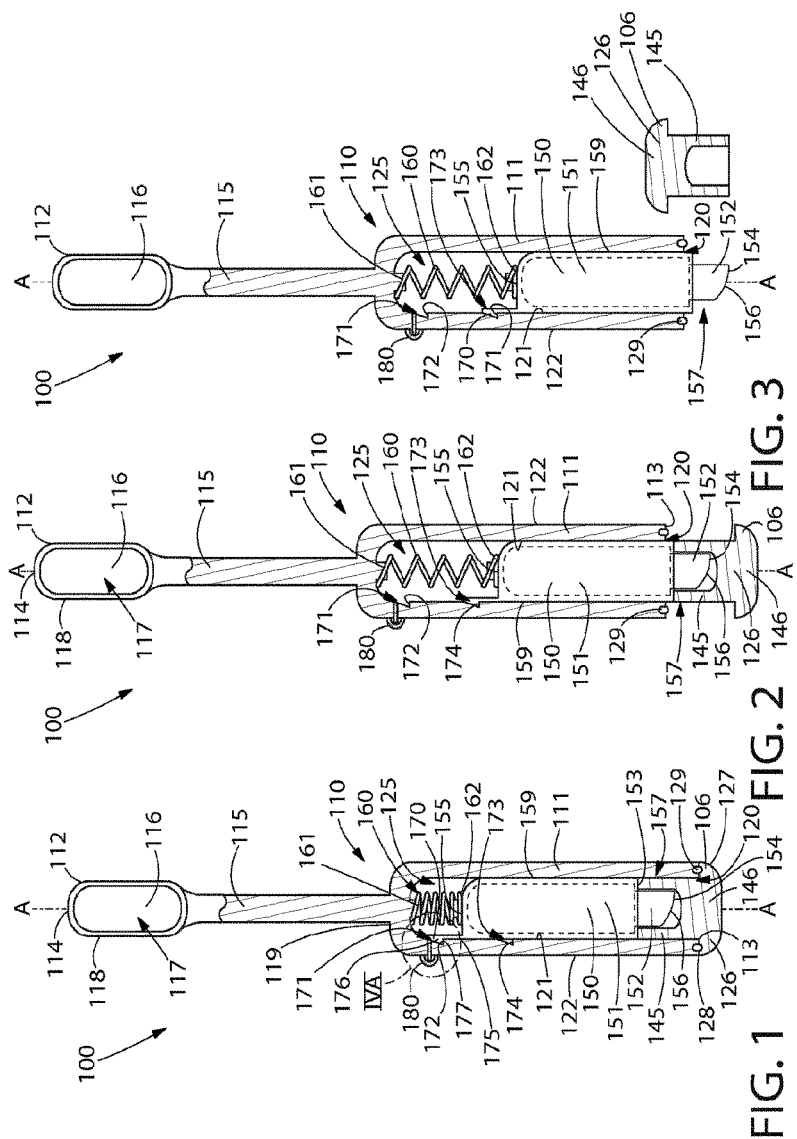

ORAL CARE SYSTEM

CROSS-REFERENCE TO RELATED PATENT APPLICATIONS

This application is a U.S. national stage application under 35 U.S.C. §371 of PCT Application No. PCT/US2012/60776, filed Oct. 18, 2012, the entirety of which is incorporated herein by reference.

FIELD OF THE INVENTION

The present invention relates generally to an oral care system, and specifically to an oral care system including a toothbrush and a dispenser.

BACKGROUND OF THE INVENTION

Oral care products or agents are applied in different ways. For example, a common technique used for tooth whitening products is to cast an impression of a person's teeth and provide a tray of the shape of this impression. While tray-based systems are suitable, many people do not use them due to the fact that they tend to be uncomfortable and/or awkward. Moreover, in order to use a whitening tray, a user must keep the tray and the required components at hand. This not only requires extra storage space in already cramped bathroom cabinets but also requires that the user remember to use the whitening system. Furthermore, these tray-based systems are not conveniently portable for transport and/or travel.

In addition to difficulties in applying some oral care products, storage is sometimes cumbersome and inconvenient for the user. The oral care product must typically be stored separately from oral care tooth cleaning implements such as a toothbrush since the oral care product package and toothbrush heretofore are generally treated as separate and distinct parts of an oral care regimen. A more portable, compact and convenient way to store oral care products, and to dispense and apply those oral care products to oral surfaces is desired.

BRIEF SUMMARY OF THE INVENTION

Embodiments of the present invention provide an efficient, compact, and portable oral care system that combines an oral care implement such as a toothbrush with an oral care product or agent dispenser in a highly portable housing. Advantageously, such embodiments are especially suited for easy transport and/or travel.

In one embodiment, the invention can be an oral care system comprising: a toothbrush body comprising a handle and a head, the toothbrush body extending along a longitudinal axis from a proximal end to a distal end; a plurality of tooth cleaning elements extending from the head; an opening in the proximal end of the toothbrush body that forms a passageway into an internal cavity of the handle; a first dispenser positioned within the internal cavity and comprising a first store of oral care material, the first dispenser resiliently coupled to the toothbrush body to be alterable between: (1) a first retracted state; and (2) a first extended state.

In another embodiment, the invention can be an oral care system comprising: a toothbrush body comprising a handle and a head; a plurality of tooth cleaning elements extending from the head; an opening in the toothbrush body that forms a passageway into an internal cavity of the handle; a first dispenser positioned within the internal cavity and comprising a first store of oral care material, the first dispenser resiliently coupled to the toothbrush body to be alterable between: (1) a first retracted state; and (2) a first extended state.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a schematic of an oral care system according to a first embodiment of the present invention including a dispenser in a retracted state within a handle internal cavity;

FIG. 2 is a schematic of the oral care system of FIG. 1 wherein the dispenser is in an extended state and a toothbrush cap is in a closed state;

FIG. 3 is a schematic of the oral care system of FIG. 1 wherein the dispenser is in an extended state and the toothbrush cap is in an open state;

DETAILED DESCRIPTION OF THE INVENTION

Figure 4A:
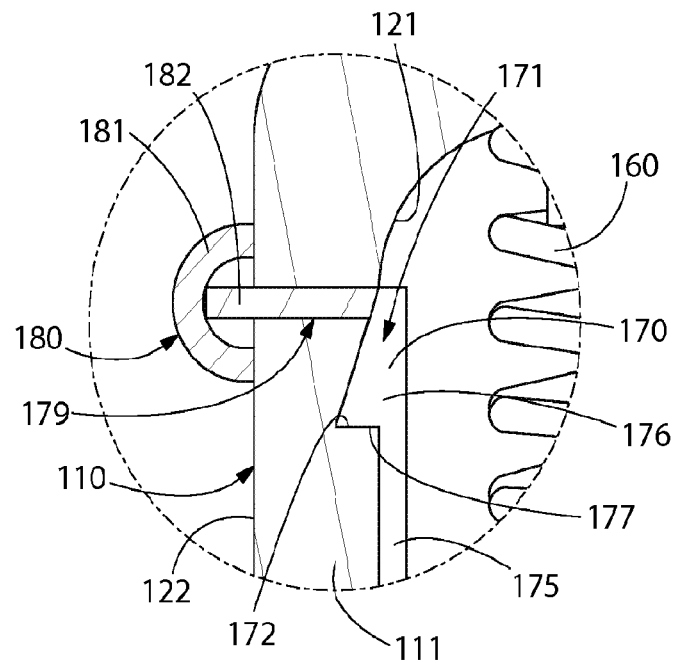
FIG. 4A is a close-up view of area IVA of FIG. 1 wherein an actuator is in a non-actuated state.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Preferred embodiments of the present invention will now be described with respect to one or more possible oral care or treatment systems. Embodiments of the oral care system include at least one dispenser that may include, without limitation, one or more of the following oral care materials: tooth whitening, antibacterial, enamel protection, anti-sensitivity, anti-inflammatory, anti-attachment, fluoride, tartar control/protection, flavorant, sensate, colorant and others. However, other embodiments of the present invention may be used to store and dispense any suitable type of oral care material and the invention is expressly not limited to any particular oral care system or oral care material alone. Furthermore, some embodiments of the oral care system include a first dispenser and a second dispenser, each of which may include any one of the oral care materials noted above. A more detailed, although still non-exhaustive, listing of possible oral care materials that may be stored in the dispenser(s) of the present invention and utilized with the oral care system will be provided below.

Referring to FIGS. 1-3, an oral care system 100 is illustrated according to one embodiment of the present invention. The oral care system 100 is a compact, readily portable, self-contained, user-friendly system that comprises all of the necessary components and chemistries for a user to perform a desired oral care treatment routine. As will be described in greater detail below, the oral care system 100 in one exemplary embodiment generally comprises a toothbrush body 110 comprising a handle 111, a head 112 and an elongated neck 115 extending between the handle 111 and the head 112. The toothbrush body 110 extends along a longitudinal axis A-A from a proximal end 113 to a distal end 114.

In the exemplified embodiment, the entire toothbrush body 110, including the handle 111, the head 112 and the elongated neck 115, is formed as a single integral piece using a molding, milling, machining or other suitable process. However, in other embodiments the handle 111 and the head 112 (and the neck 115) may be formed as separate components which are operably connected at a later stage of the manufacturing process by any suitable technique known in the art including without limitation thermal or ultrasonic welding, a tight-fit assembly, a coupling sleeve, threaded engagement, adhesion, or fasteners.

In certain embodiments, the toothbrush body 110 is formed of a rigid plastic material, such as for example without limitation polymers and copolymers of ethylene, propylene, butadiene, vinyl compounds and polyesters such as polyethylene terephthalate. However, the invention is not to be so limited in all embodiments and in certain other embodiments the toothbrush body 110 can be formed of other materials. Furthermore, in some embodiments the handle 111 of the toothbrush body 110 may be overmolded with a soft, resilient material, such as a thermoplastic elastomer, to provide comfort to a user when gripping the handle 111 during use of the oral care system 100 to clean and/or sanitize a user's oral cavity.

In the exemplified embodiment, the toothbrush body 110 (i.e., the handle 111, the neck 115 and the head 110) forms a manual toothbrush that is typically used to brush a user's teeth. However, the invention is not to be so limited in all embodiments and in certain other embodiments the toothbrush body 110 can be any other type of oral care implement, such as for example without limitation, a powered toothbrush, a tongue scraper, a gum and soft tissue cleanser, a water pick, an interdental device, a tooth polisher, a specially designed ansate implement having tooth engaging elements specially designed to increase the effect of an active agent on the teeth or any other type of implement that is commonly used for oral care. Thus, it is to be understood that the inventive concepts discussed herein can be applied to any type of oral care implement unless a specific type of oral care implement is specified in the claims.

In the exemplified embodiment, the head 112 of the toothbrush body 110 is generically illustrated as being ovular in shape. However, the invention is not to be so limited and the head 112 of the toothbrush body 110 can take on any other desired shape. Furthermore, in the exemplified embodiment the head 112 of the toothbrush body 110 has a plurality of tooth cleaning elements 116 extending therefrom. More specifically, the head 112 of the toothbrush body 110 comprises a front surface 117 and an opposite rear surface 118, and the tooth cleaning elements 166 extend outwardly from the front surface 116.

The exact structure, pattern, orientation and material of the tooth cleaning elements 116 is not to be limiting of the present invention unless so specified in the claims. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 116 of the present invention can be connected to the head 112 of the toothbrush body 110 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In certain embodiments, the head 112 of the toothbrush body 110 may also include a soft tissue cleanser coupled to or positioned on the rear surface 118 of the head 112, which is opposite the front surface 117 from which the tooth cleaning elements 116 extend. An example of a suitable soft tissue cleanser that may be used with the present invention is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the head 112 of the toothbrush body 110 may not include any soft tissue cleanser.

The handle 111 of the toothbrush body 110 extends from the proximal end 113 of the toothbrush body 110 to a distal end 119 of the handle 111. The distal end 119 of the handle 111 is the portion of the handle 111 from which the neck 115 and/or head 112 extends. The handle 111 comprises an inner surface 121 and an outer surface 122. The outer surface 122 of the handle 111 forms a gripping surface of the toothbrush body 110. Thus, the handle 111 is an elongated structure that provides the mechanism by which a user can hold and manipulate the toothbrush body 110 during use.

The inner surface 121 of the handle 111 defines an internal cavity 125. Furthermore, an opening 120 is formed into the proximal end 113 of the toothbrush body 110. The opening 120 forms a passageway into the internal cavity 125 of the handle 111. Thus, the opening 120 provides access into the internal cavity 125 from an area external to the internal cavity 125. In the exemplified embodiment, the opening 120 is located on the opposite end of the handle 111 relative to the location from which the neck 115 and/or head 112 extends. However, the invention is not to be so limited and the opening 120 can be otherwise located, such as into a side surface of the handle 111 or into the same side of the handle 111 from which the neck 115 and/or head extends 112 as desired.

The oral care system 100 further comprises a dispenser 150 positioned within the internal cavity 125. The dispenser 150 extends from a proximal end 155 to a distal end 154. In certain embodiments the dispenser 150, including the structural details and means for dispensing oral care material, may be similar to that disclosed in U.S. patent application Ser. No. 13/518,424, filed on Jun. 22, 2012, the entirety of which is incorporated herein by reference. In some embodiments, the dispenser 150 can be a pen-type dispenser. However, the invention is not to be so limited in all embodiments and the dispenser 150 can take on other structural forms including those discussed herein below.

The dispenser 150 comprises a first store of oral care material. More specifically, the dispenser 150 has an internal cavity or reservoir that holds the first store of oral care material therein for dispensing. The different types of oral care material that can be used as the first store of oral care material and contained within the dispenser 150 will be described in more detail below. The dispenser 150 is resiliently coupled to the toothbrush body 110 so as to be alterable between a retracted state, as illustrated in FIG. 1, and an extended state, as illustrated in FIGS. 2 and 3. The dispenser 150 comprises a dispenser body 151 and an applicator 152. Specifically, the applicator 152 extends from the dispenser body 151. The applicator 152 is not as wide as the dispenser body 151, and therefore a shoulder 153 is formed on the portion of the dispenser body 151 from which the applicator 152 extends.

The dispenser body 151 of the dispenser 150 is an elongated structure having an inner surface that defines a hollow interior cavity for storing the first store of oral care material therein. Furthermore, the dispenser body 151 has an outer surface 159. In the exemplified embodiment, when the dispenser 150 is located within the internal cavity 125 of the handle 111, the outer surface 159 of the dispenser 150 is in surface contact with the inner surface 121 of the handle 111. However, the invention is not to be so limited and in other embodiments a gap may be formed between the outer surface 159 of the dispenser 150 and the inner surface 121 of the handle 111. Regardless of whether there is a gap or not, the dispenser 150 is capable of movement within the internal cavity 125 between the retracted and extended states, so any surface contact between the outer surface 159 of the dispenser 150 and the inner surface 121 of the handle 111 must not impede such movement of the dispenser 150, which will be described in more detail below.

In certain embodiments, the dispenser body 151 has a cross-sectional profile that corresponds to the cross-sectional profile of the cavity 125. Furthermore, in certain embodiments the outer surface 159 of the dispenser body 151 is circular. In such embodiments, the inner surface 121 of the handle 111 and/or the outer surface 159 of the dispenser body 151 may include grooves and/or protrusions to prevent relative rotation between the dispenser 150 and the toothbrush body 110. In other embodiments, the cross-sectional profiles of the cavity 125 and the dispenser body 151 can be non-circular to prevent relative rotation between the dispenser 150 and the toothbrush body 110. Furthermore, the resilient element 160 may also assist in preventing relative rotation between the dispenser 150 and the toothbrush body 110.

A dispensing orifice 156 is formed into the applicator 152 at the distal end 154 of the dispenser 150. A user can apply the first store of oral care material by squeezing, compressing or otherwise forcing the first store of oral care material from the dispenser 150 and out of the dispensing orifice 156 in the distal end 154 of the dispenser 150. As will be appreciated from the discussion below with regard to FIG. 3, in certain embodiments the dispenser body 151 remains positioned or located within the internal cavity 125 even during dispensing such that only the applicator 152 protrudes through the opening 120. In such embodiments, the entire handle 111 of the toothbrush body 110 may be compressible for facilitating dispensing of the first store of oral care material from the dispenser 150. In other embodiments, the oral care system 100 may include a threaded screw coupled to an elevator mechanism for forcing the oral care material from the dispenser 150 out through the dispensing orifice 156. Such a threaded screw/elevator mechanism could be coupled to the dispenser 150 on a portion of the dispenser 150 that protrudes from the opening 120 when the dispenser 150 is in the extended state. Of course, any other mechanisms that assist with dispensing, such as mechanical, electrical, or electromechanical pumps and the like, can be used in other embodiments.

Furthermore, in some embodiments upon the dispenser 150 achieving the extended state, the dispenser 150 may automatically dispense a pre-determined amount of the oral care material. In such embodiments, the oral care material may be dispensed at a delay after the dispenser 150 achieves the extended state in order to enable a user to prepare for application of the oral care material onto his or her teeth and other oral surfaces. Such an embodiment would include the necessary processor and memory. In still other embodiments, the applicator 152 may include a dispensing chamber that is in fluid communication with a reservoir that contains the oral care material. The applicator 152 can be compressible such that upon compressing the applicator 152 downwardly in a direction towards the dispenser body 151, the oral care material is dispensed. In still other embodiments, dispensing of the oral care material can be achieved via capillary action or wicking. In such an embodiment, a capillary material is positioned within the dispenser 150 in contact with the oral care material and is exposed through the dispensing orifice 156 of the dispenser 150. A user can apply the oral care material by contacting the exposed portion of the capillary material to the user's teeth or other oral surfaces.

In certain embodiments, the dispenser 150 may be refillable so that a user can refill the first store of oral care material into the dispenser 150 after depletion thereof. However, in certain other embodiments upon depletion of the first store of oral care material contained within the dispenser 150, the entire oral care system 100 will be replaced. Thus, in certain embodiments the amount of the first store of oral care material contained within the dispenser 150 is indicative of the life-cycle of the tooth cleaning elements 116 (i.e., the first store of oral care material may last for three months when used regularly, which is the time period recommended for replacement of a toothbrush).

In certain embodiments, the applicator 152 may be formed of an elastomeric material to provide comfort when applying the oral care material directly onto a user's teeth and/or oral surfaces from the dispenser 150. Specifically, when dispensing the oral care material directly onto a tooth, the applicator 152 can be made to contact the tooth directly to ensure that the oral care material is adequately and sufficiently applied onto the tooth surface. Forming the applicator 152 out of an elastomeric material makes this direct dispensing process more comfortable for a user. However, the invention is not to be so limited and in certain other embodiments the applicator 152 may be formed of other materials, including bristles, a porous or sponge material, or a fibrillated material. Furthermore, in still other embodiments the applicator 152 may be omitted and the dispensing orifice 156 can be formed directly into the dispenser 150 for dispensing the oral care material contained therein.

In the exemplified embodiment, the applicator 152 has an angled top surface. Angling the top surface makes it easier to apply the oral care material directly to a user's teeth. However, the invention is not to be so limited in all embodiments and in certain other embodiments the top surface of the applicator 152 can be a flat surface, or it can have various contours to match the contours of a user's teeth and/or other oral surfaces.

As noted above, the dispenser 150 is alterable between a retracted state and an extended state. More specifically, a resilient element 160 is fixed within the internal cavity 125 that is capable of altering the dispenser 150 between the retracted and extended states. The resilient element 160 has a first portion 161 that is fixed to the inner surface 121 of the handle 111 of the toothbrush body 110 and a second portion 162 that is fixed to the proximal end 155 of the dispenser 150. In the exemplified embodiment, the first portion 161 of the resilient element 160 is fixed to a protrusion extending downwardly from a roof of the internal cavity 125 and the second portion 162 of the resilient element 160 is fixed to a protrusion extending from the proximal end 155 of the dispenser 150. However, the invention is not to be so limited and the resilient element 160 can be fixed at other locations or in other manners to the dispenser 150 and the toothbrush body 110 and still achieve the same effect as discussed herein.

In the exemplified embodiment, the resilient element 160 is a compression spring. However, the invention is not to be so limited and the resilient element 160 can take on other forms, including without limitation a torsion spring, an extension spring, a barrel spring, a coil spring, a drawbar spring, a magazine spring, a spring pin, a cotter pin, an air spring, a gas spring, a leaf spring, a cantilever spring, a volute spring, a rubber spring, a spring washer, a wave spring or the like. The resilient element 160 need not be a spring in all embodiments and can be any element that enables the dispenser 150 to be alterable between the retracted state and the extended state, as will be discussed in more detail below. For example without limitation, the resilient element 160 can simply be a manual slide that enables a user to slide the dispenser 150 into and out of the internal cavity 125 between the retracted and extended states.

Referring now solely to FIG. 1, the oral care system 100 will be further described with regard to the dispenser 150 being in the retracted state. When the dispenser 150 is in the retracted state, an entirety of the dispenser 150 is located within the internal cavity 125. The dispenser 150 comprises a locking element 170 for locking the dispenser 150 in the retracted state. The locking element 170 extends from the proximal end 155 of the dispenser 150 in an axial direction towards the head 112 of the toothbrush body 110. More specifically, the locking element 170 comprises a rod portion 175 and a locking portion 176. The rod portion 175 is an elongated structure that extends from the proximal end 155 of the dispenser 150. The locking portion 176 extends from the rod portion 175 and has an engaging surface 177 that facilitates achieving and maintaining the retracted state of the dispenser 150 as will be discussed in more detail below. When the dispenser 150 is in the retracted state, the rod portion 175 of the locking element 170 abuts against and is in surface contact with the inner surface 121 of the handle 111.

The inner surface 121 of the handle 111 has a depression 171 formed therein. The depression 171 is a groove, dimple or notch formed into the inner surface 121 of the handle 111. The depression 171 can take on any shape as long as it can maintain the dispenser 150 in the retracted state as discussed below. In the exemplified embodiment, the depression 171 comprises a shoulder 172. In the exemplified embodiment, the inner surface 121 of the handle 111 also comprises a stop notch 173 having a shoulder 174. The stop notch 173 is similar in size and shape to the depression 171. The purpose of the stop notch 173 will be better understood from the discussion of FIGS. 2 and 3 below.

The locking element 170 is alterable between a locking state and a released state, which will be discussed in more detail below with reference to FIGS. 4A and 4B. When the dispenser 150 is in the retracted state, the locking element 170 is in the locking state whereby the locking member 170 nests within the depression 171 and engages the shoulder 172 of the depression 171. Due to the interaction between the locking member 170 and the depression 171, and more specifically between the engaging surface 177 of the locking portion 176 of the locking member 170 and the shoulder 172 of the depression 171, the dispenser 150 is maintained in the retracted state whereby the dispenser 150 is positioned within the internal cavity 125.

The dispenser 150 has a distal portion 157, which includes the shoulder 153 and the applicator 152. The distal portion 157 of the dispenser 150 comprises a dispenser cap 126 coupled to the dispenser body 151 of the dispenser 150. The dispenser cap 126 is alterable between a closed state in which the dispenser cap 126 covers the dispensing orifice 156 (FIGS. 1 and 2) and an open state in which the first dispensing orifice 156 is exposed (FIG. 3).

When the dispenser 150 is in the retracted state and the dispenser cap 126 is coupled to the dispenser (FIG. 1), the dispenser cap 126 abuts the proximal end 113 of the toothbrush body 110 and covers the opening 120. Furthermore, when the dispenser 150 is in the retracted state and the dispenser cap 126 is coupled to the dispenser 150, a first portion 145 of the dispenser cap 126 is located within the internal cavity 125 and a second portion 146 of the dispenser cap 126 extends from the proximal end 113 of the handle 111 and blocks the opening 120. Thus, the dispenser cap 126 prevents access from the external environment into the cavity 125 through the opening 120. The dispenser cap 126 comprises an outer surface 127. When the dispenser cap 126 is coupled to the toothbrush body 110 and the dispenser 150 is in the retracted state, the outer surface 127 of the dispenser cap 126 and the outer surface 122 of the handle 111 form a smooth continuous surface at an interface 128 between the dispenser cap 126 and the handle 111. The dispenser cap 126 can be coupled to the dispenser body 110 using any desired technique, including a snap-fit, an interference fit, threaded screws, fasteners or the like.

Furthermore, in the exemplified embodiment an O-ring 129 is coupled to the proximal end 113 of the toothbrush body 110. The dispenser cap 126 has a flange portion 106 that abuts against the proximal end 113 of the toothbrush body 110 when the dispenser cap 126 is coupled to the toothbrush body 110. Thus, the O-ring 129 acts as a seal that becomes compressed between the flange portion 106 of the dispenser cap 126 and the proximal end 113 of the toothbrush body 110 when the dispenser cap 126 is coupled to the toothbrush body 110. As a result, a fluid-tight seal is formed that prevents debris and liquids from entering into the internal cavity 125. The O-ring can be any type of gasket or seal that facilitates creating a seal between the dispenser cap 126 and the toothbrush body 110. The dispenser cap 126 also seals and protects the applicator 152, and more specifically the dispensing orifice 156 of the dispenser 150 to prevent the store of oral care material contained within the dispenser 150 from prematurely drying out or from being accidently dispensed.

The oral care system 100 further comprises an actuator 180 that is coupled to the locking element 170. The actuator 180 is alterable between a non-actuated state (FIG. 4A) and an actuated state (FIG. 4B). Furthermore the actuator is biased into the non-actuated state.

Figure 4B:
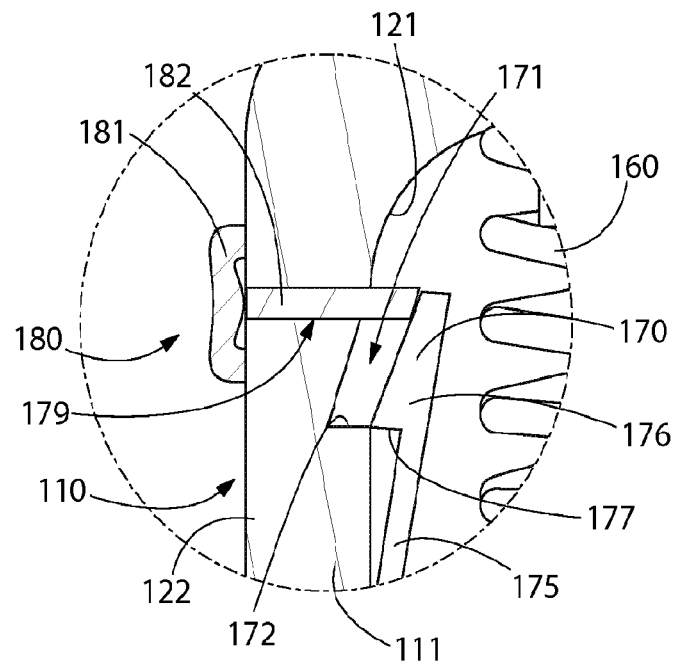
FIG. 4B is the close-up view of FIG. 4A wherein the actuator is in an actuated state.

Referring to FIGS. 4A and 4B, the actuator 180 and the locking element 170 will be further described. In the exemplified embodiment, the actuator 180 comprises a depressible button 181 and a rod 182. The rod 182 extends through a channel 179 that is formed into the handle 111. The channel 179 extends from the outer surface 122 of the handle 111 to the inner surface 121 of the handle 111. The rod 182 has a length that is greater than the length of the channel 179 so that a portion of the rod 182 can either extend through the opening into the channel 179 on the outer surface 122 of the handle 111 or the opening of the channel 179 on the inner surface 121 of the handle 111. This feature enables the rod 182 to engage the locking element 170 as will be discussed below to force the locking element 170 into the released state, which in turn forces the dispenser 150 from the retracted state into the extended state.

In the exemplified embodiment the rod 182 is coupled to the depressible button 181, and in certain embodiments may be integrally formed with the depressible button 181. In FIG. 4A, the actuator 180 is in its biased, non-actuated state. In this state, the locking element 170 is positioned within the depression 171 such that the locking element 170 engages the shoulder 172 of the depression 171. More specifically, the engaging surface 177 of the locking portion 176 of the locking element 170 abuts against and engages the shoulder 172 of the depression 171 when the locking element 170 is in the locked state and the dispenser 150 is in the retracted state.

Upon a user depressing the depressible button 181, the rod 182 contacts the locking element 170 and pushes it in a direction transverse to the longitudinal axis A-A such that the locking element 170 is removed from the depression 171. The locking element 170 is a resilient component such that it is capable of flexing into and out of the depression 171 as discussed herein while remaining connected to the proximal end 155 of the dispenser 150. The locking element 170 may be formed out of a plastic material such as has been discussed herein above, but it is thin enough so as to maintain flexibility and resiliency in order to achieve its desired function. In other embodiments the locking element 170 may be formed out of an elastomeric material, a resilient metal, or any other material so long as it can function as described herein.

The locking element 170 is self-biased into the locked state such that the locking element 170 is biased into a position whereby the locking element 170 is nested within the depression 171 when the dispenser 150 is in the retracted state. However, upon the user depressing the depressible button 181 and thereby actuating the actuator 180, the locking element 170 is pushed out of its biased position and into the released state due to the resiliency of the locking element 170. Thus, actuation of the actuator 180 forces the locking element 170 into the released state, which is illustrated in FIG. 4B. Furthermore, actuation of the actuator 180 causes at least a portion of the rod portion 175 of the locking element 170 to come out of contact with the inner surface 121 of the handle 111.

FIG. 4B illustrates the locking element 170 just as it reaches the released state and before the resilient element 160 has used its biasing force to alternate the dispenser 150 into the extended state. Thus, upon the locking element 170 achieving the released state, the dispenser 150 is automatically biased into the extended state due to the resilient element 160 as will be discussed in more detail below with reference to FIGS. 2 and 3. Furthermore, after depressing and releasing the actuator 180, the actuator 180 returns to its non-actuated state due to it being biased into the non-actuated state. In certain embodiments, the actuator 180 only returns to its non-actuated state upon the dispenser 150 being returned to the retracted state due to the locking element 170 pushing the rod portion 182 into the channel 179 in the direction of the button 181.

Although described and illustrated herein as being a depressible button 181, the actuator 180 is not limited to such a structure. The actuator 180 can be any type of mechanism that is capable of altering the locking element 170 between its biased locked state and the released state. For example without limitation, the actuator 180 may be a switch, a slide lock, a pull pin, a push pin, a magnetic actuator system, or any other type of mechanism capable of achieving the function described herein.

Referring now to FIG. 2, the oral care system 100 will be described after the actuator 180 has been actuated. Upon actuating the actuator 180 (by depressing the depressible button 181 as described above, or in any other manner), the locking element 170 is forced into the released state and the dispenser 150 translates from the retracted state into the extended state. The dispenser 150 is actually biased into the extended state due to the bias of the resilient element 160. When moving between the retracted state and the extended state (and vice versa), the dispenser 150 translates along a first path that is substantially parallel to the longitudinal axis A-A.

As the dispenser 150 translates from the retracted state to the extended state, the locking element 170, and more specifically the locking portion 176 of the locking element 170, pushes against the inner surface 121 of the handle 111 due to its bias/resiliency. Thus, upon the locking element 170, and more specifically the locking portion 176 of the locking element 170, reaching the stop notch 173, the locking portion 176 of the locking element 170 enters into the stop notch 173 such that the engaging surface 177 of the locking portion 176 of the locking element 170 abuts against the shoulder 174 of the stop notch 173. Furthermore, upon reaching this position, the rod portion 175 of the locking element 170 again abuts against and is in surface contact with the inner surface 121 of the handle 111. Thus, the combination of the stop notch 173 and the locking element 170 prevents the dispenser 150 from being completely disengaged and/or separated from the handle 111.

Thus, the oral care system 100 comprises a stopper element or retaining element that prevents over-extension of the dispenser 150 beyond the extended state and prevents the dispenser 150 from being completely detached from the toothbrush body 110. In the exemplified embodiment, the locking element 170 acts as the stopper element due to it being biased into the stop notch 173 and engaging the shoulder 174 thereof. However, the invention is not to be so limited in all embodiments. In certain other embodiments the dispenser 150 may include a shoulder or flange that is separate from the locking element 170 such that the shoulder or flange engages a protrusion extending from the inner surface 121 of the handle 111 to prevent over-extension of the dispenser 150. In such embodiments, after the locking element 170 is removed from the depression 171, the dispenser 150 will translate into the extended position until the flange or shoulder of the dispenser 150 contacts the protrusion extending from the inner surface 121 of the handle 111. Other mechanisms and structures are contemplated for acting as the stopper element or retaining element to prevent over-extension of the dispenser 150 beyond the extended state and to thereby prevent the dispenser 150 from being completely detached from the toothbrush body 110. For example, any combination of grooves, notches, flanges, protrusions, protuberances or other mechanical structures can be used. Alternatively, electrical locking systems can be used to prevent over-extension of the dispenser 150 as desired. These stopper/retaining elements also prevent over-extension of the resilient element 160, which could cause the resilient element to become non-functional (such as when a spring is over-extended and is therefore no longer capable of achieving its intended function).

In the exemplified embodiment, upon the dispenser 150 achieving the extended state, the locking element 170 nests within the stop notch 173 as discussed above. Furthermore, when the dispenser 150 is in the extended state, the distal portion 157 of the dispenser 150 protrudes from and through the opening 120. As discussed above, the distal portion 157 of the dispenser 150 includes the applicator 152 and the dispensing orifice 156. Thus, in the extended state the dispensing orifice 156 of the dispenser 150 protrudes through the opening 120 and is accessible to a user so that the user can apply the oral care material contained within the dispenser 150 to the user's teeth and other oral surfaces using the dispensing techniques described herein above and others.

In FIG. 2, the dispenser 150 is in the extended state and the dispenser cap 126 remains coupled to the dispenser body 151 of the dispenser 150. Thus, the dispenser cap 126 is attached to the dispenser body 151 and therefore moves axially with the dispenser 150 as the dispenser 150 alternates between the retracted and extended states. When a user desires to use the dispenser 150 to dispense the oral care material therefrom, the user first removes the dispenser cap 126 from the dispenser body 151, which can be achieved simply by pulling on the dispenser cap 126 in an axial direction away from the toothbrush body 110. Upon removing the dispenser cap 126 from the dispenser body 151, the oral care material can be dispensed from the dispenser 150 through the dispensing orifice 156. The oral care system 100 is illustrated with the dispenser 150 in the extended state and with the dispenser cap 126 removed or separated from the dispenser body 151 in FIG. 3.

Figure 5:
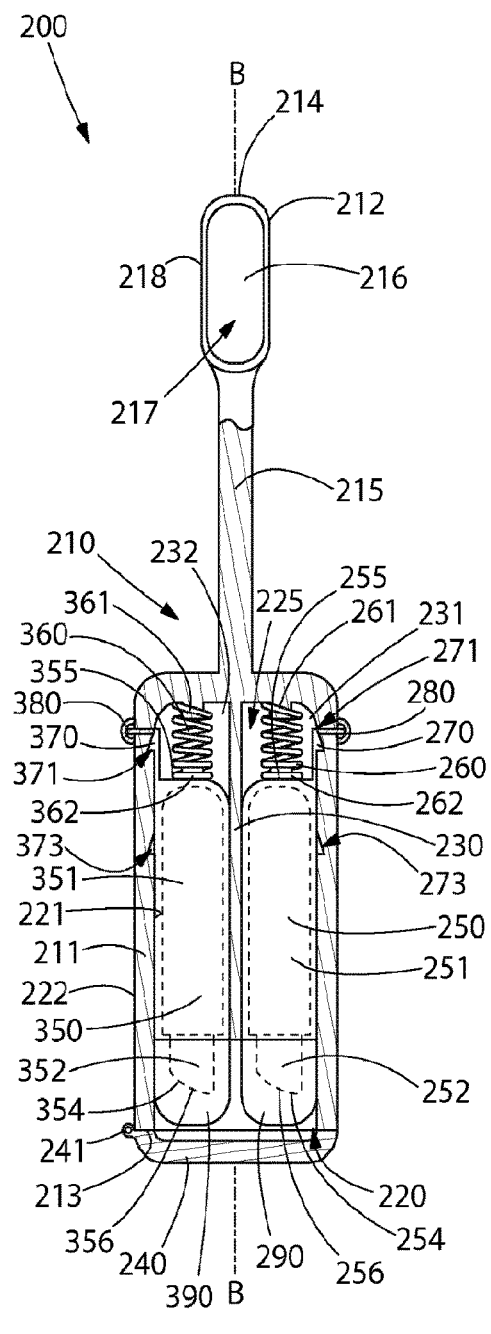
FIG. 5 is a schematic of an oral care system according to a second embodiment of the present invention including multiple dispensers in a retracted state within a handle internal cavity.
Figure 6:
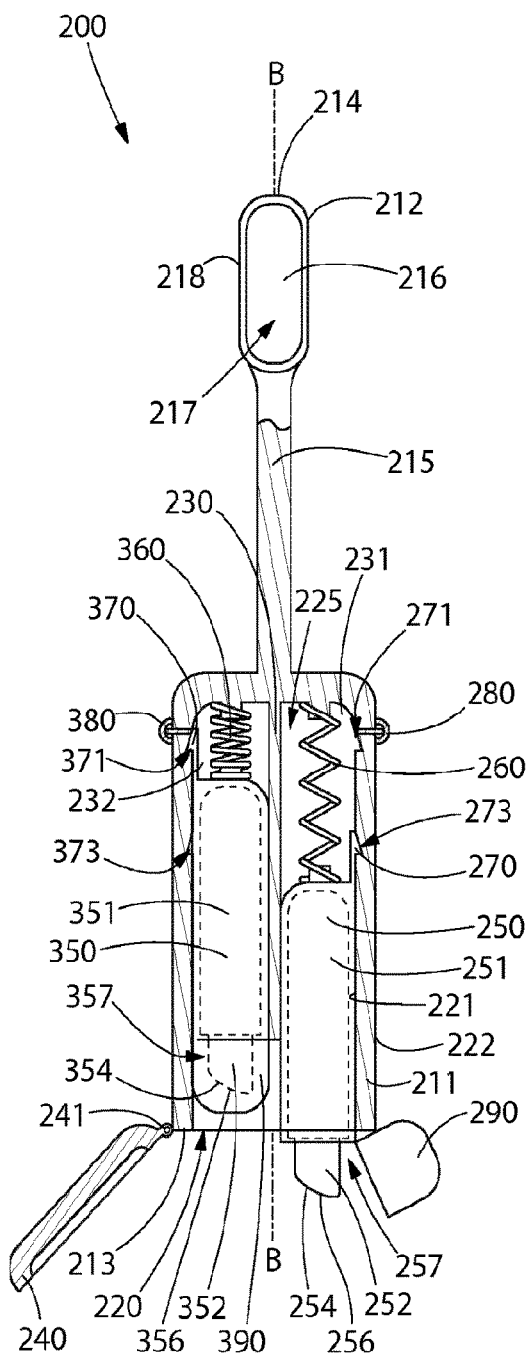
FIG. 6 is a schematic of the oral care system of FIG. 5 wherein one of the dispensers is in an extended state.

Referring to FIGS. 5 and 6, an oral care system 200 will be described in accordance with a second embodiment of the present invention. The oral care system 200 is similar to the oral care system 100 except that the oral care system 200 includes a first dispenser 250 and a second dispenser 350. Many of the features of the first dispenser 250 and the second dispenser 350 are similar to the features of the dispenser 150 discussed above with regard to the oral care system 100. Furthermore, the oral care system 200 includes a toothbrush body 210 having a handle 211 and a head 212. Many features of the toothbrush body 210 are similar to the features of the toothbrush body 110 of the oral care system 100 described above. Similar features of the oral care system 200 will not be described herein below in detail in the interest of brevity. However, similar features of the oral care system 200 will be similarly numbered to the corresponding feature from the oral care system 100 except that the 200-series and 300-series of numbers will be used. Where a detailed description of a component of the oral care system 200 is not provided, the description of the similar component of the oral care system 100 will apply.

As noted above, the oral care system 200 comprises the toothbrush body 210 having the handle 211 and the head 212. Furthermore, a neck 215 extends between the handle 211 and the head 212. The head 212 has a front surface 217 and an opposing rear surface 218. Tooth cleaning elements 216, such as any of the various types of tooth cleaning elements described above, extend from the front surface 217 of the head 211. Although not illustrated, a soft tissue cleanser may be positioned on the rear surface 218 of the head 211, which can include any soft tissue cleanser described above. The toothbrush body 210 extends along a longitudinal axis B-B from a proximal end 213 to a distal end 214.

The handle 211 of the toothbrush body 210 has an inner surface 221 and an outer surface 222. The inner surface 221 of the handle 211 defines an internal cavity 225. A divider wall 230 extends into the internal cavity 225 from a roof of the internal cavity 225 to separate the internal cavity 225 into a first chamber 231 and a second chamber 232. In the exemplified embodiment, the divider wall 230 extends into the internal cavity 225 a distance that is greater than half of the length of the internal cavity 225. However, the invention is not to be so limited and the divider wall 201 may extend less distance into the internal cavity 225 from the roof of the internal cavity 225. Furthermore, in still other embodiments the divider wall 230 may be omitted and the internal cavity 225 may not be separated into two chambers.

An opening 220 is formed into the toothbrush body 210 at the proximal end 213 of the toothbrush body 210. The opening 220 forms a passageway into the internal cavity 225, and more specifically into each of the first and second chambers, 231, 232 of the internal cavity 225 from the external environment. In the exemplified embodiment, a toothbrush cap 240 is coupled to the toothbrush body 210 at the proximal end 213 of the toothbrush body 210. The toothbrush cap 240 is alterable between a closed state, as illustrated in FIG. 5, in which the toothbrush cap 240 covers the opening 220, and an open state, as illustrated in FIG. 6, in which the toothbrush cap 240 does not cover the opening 220 and the opening 220 is exposed. In the exemplified embodiment, the toothbrush cap 240 is coupled to the toothbrush body 210 by a hinge 241. In certain embodiments, the hinge 241 may include a resilient member or spring that biases the toothbrush cap 240 into the closed position. However, the invention is not to be so limited and in certain other embodiments the toothbrush cap 240 can be coupled to the toothbrush body 210 by other means, including a tight fit, an interference fit, threaded screws, fasteners, magnets or the like. Furthermore, in still other embodiments the toothbrush cap 240 can be altogether omitted and the opening 220 may always remain exposed.

As discussed above, the oral care system 200 comprises the first dispenser 250 and the second dispenser 350. The first dispenser 250 contains a first store of oral care material therein. The second dispenser 350 contains a second store of oral care material therein. In certain embodiments, the first store of oral care material is different than the second store of oral care material. However, the invention is not to be so limited in all embodiments and in certain other embodiments each of the first and second stores of oral care material can be the same.

The first dispenser 250 is positioned within the first chamber 231 and the second dispenser 350 is positioned within the second chamber 232. Thus, in the exemplified embodiment the first and second dispensers 250, 350 are separated from one another by the divider wall 230 along at least a portion of their length. The first dispenser 250 extends from a proximal end 255 to a distal end 254 and the second dispenser 350 extends from a proximal end 355 to a distal end 354. The first dispenser 250 is resiliently coupled to the toothbrush body 210 to be alterable between a first retracted state (FIG. 5) and a first extended state (FIG. 6). The second dispenser 350 is resiliently coupled to the toothbrush body 210 to be alterable between a second retracted state (FIG. 5) and a second extended state (not illustrated).

A first resilient element 260 is positioned within the first chamber 231 to facilitate the first dispenser 250 alternating between the first retracted state and the first extended state. The first resilient element 260 has a first portion 261 that is fixed to the toothbrush body 210 (specifically at the roof of the first chamber 231) and a second portion 262 that is connected to the proximal end 255 of the first dispenser. A second resilient element 360 is positioned within the second chamber 232 to facilitate the second dispenser 350 alternating between the second retracted state and the second extended state. The second resilient element 360 has a first portion 361 that is fixed to the toothbrush body 210 (specifically at the roof of the second chamber 232) and a second portion 362 that is connected to the proximal end 355 of the second dispenser 350. The first and second resilient elements 260, 360 have a similar structure and function to the resilient element 160 of the oral care system 100.

The first dispenser 250 comprises a first locking element 270 for locking the first dispenser 250 in the retracted state whereby the first dispenser 250 is entirely contained within the internal cavity 225, and more specifically within the first chamber 231 of the internal cavity 225. The first locking element 270 engages a first depression or notch 271 formed into the inner surface 221 of the handle 211 in the same manner as has been discussed above with regard to the oral care system 100. The inner surface 221 of the handle 211 further comprises a first stop notch 273 for preventing over-extension of the first dispenser 250 when the first dispenser 250 moves from the retracted state to the extended state. The details of the interaction between the first locking element 270 and the first depression or notch 271 and between the first locking element 270 and the first stop notch 273 will not be discussed herein with an understanding that the description of the same components in the oral care system 100 applies.

A first actuator 280 is operably coupled to the first locking element 270 when the first dispenser 250 is in the retracted state. Actuation of the first actuator 280 causes the first locking element 270 to disengage from the first depression or notch 271. When the first locking element 270 disengages from the first depression or notch 271, the first resilient element 260 forces the first dispenser 250 into the first extended state due to the bias of the first resilient element 260. Thus, upon actuating the first actuator 280 (which can be achieved in any of the manners discussed above with regard to the actuator 180), the first locking element 270 is released from the first depression or notch 271 and the first dispenser 250 is automatically biased into the first extended state (illustrated in FIG. 6). In the exemplified embodiment, upon being biased into the first extended state, the first locking element 270 engages the first stop notch 273 to prevent over-extension of the first dispenser 250 beyond the first extended state and to prevent the first dispenser 250 from being completely detached from the toothbrush body 210.

The second dispenser 350 comprises a second locking element 370 for locking the second dispenser 350 in the retracted state whereby the second dispenser 350 is entirely contained within the internal cavity 225, and more specifically within the second chamber 232 of the internal cavity 225. The second locking element 370 engages a second depression or notch 371 formed into the inner surface 221 of the handle 211 in the same manner as has been discussed above with regard to the oral care system 100. The inner surface 221 of the handle 211 further comprises a second stop notch 373 for preventing over-extension of the second dispenser 350 when the second dispenser 350 moves from the retracted state to the extended state. The details of the interaction between the second locking element 370 and the second depression or notch 371 and between the second locking element 370 and the second stop notch 373 will not be discussed herein with an understanding that the description of the same components in the oral care system 100 applies.

A second actuator 380 is operably coupled to the second locking element 370 when the second dispenser 350 is in the retracted state. Actuation of the second actuator 380 causes the second locking element 370 to disengage from the second depression or notch 371. When the second locking element 370 disengages from the second depression or notch 371, the second resilient element 360 forces the second dispenser 350 into the second extended state due to the bias of the second resilient element 360. Thus, upon actuating the second actuator 380 (which can be achieved in any of the manners discussed above with regard to the actuator 180), the second locking element 370 is released from the second depression or notch 371 and the second dispenser 350 is automatically biased into the second extended state. In the exemplified embodiment, upon being biased into the second extended state, the second locking element 370 engages the second stop notch 373 to prevent over-extension of the second dispenser 350 beyond the second extended state and to prevent the second dispenser 350 from being completely detached from the toothbrush body 210.

The first dispenser 250 is biased into the first extended state due to the bias of the first resilient member 260 and the second dispenser 350 is biased into the second extended state due to the bias of the second resilient element 360. Thus, in order to retain the first and second dispensers 250, 350 in the first and second retracted states within the first and second chambers 231, 232, respectively, the bias of the first and second resilient elements 260, 360 must be overcome by pressing the first and second dispensers 250, 350 in the axial direction towards the head 212 until the first and second locking elements 270, 370 engage the first and second depressions/notches 271, 371.

When the first and/or second dispensers 250, 260 are alternated into the first and second extended states, the distal portions 257, 357 of the first and second dispensers 250, 350 may contact the toothbrush cap 240 (if the toothbrush cap 240 has not previously been opened to expose the opening 220). In such embodiments, the force of the first and second dispensers 250, 350 bumping against the toothbrush cap 240 may cause the toothbrush cap 240 to open automatically.

The first and second dispensers 250, 350 are movable independent of one another. Specifically, actuating the first actuator 280 when the first dispenser 250 is in the first retracted state will cause the first dispenser 250 to be released from the first retracted state and to be biased into the first extended state. However, actuating the first actuator 280 will not cause the second dispenser 350 to move. Similarly, actuating the second actuator 380 when the second dispenser 350 is in the second retracted state will cause the second dispenser 350 to be released from the second retracted state and to be biased into the second extended state. However, actuating the second actuator 380 will not cause the first dispenser 250 to move. Thus, each of the first and second dispensers 250, 350 can be extended and used independently of one another.

The first dispenser 250 comprises a first dispenser cap 290 coupled to the first dispenser body 251 of the first dispenser 250. Specifically, the first dispenser cap 290 is coupled to the first dispenser body 251 such as by a tight fit, an interference fit, a threaded screw, fasteners or the like. The first dispenser cap 290 covers the first applicator 252 and the first dispensing orifice 256 when coupled to the first dispenser body 251. Thus, the first dispenser cap 290 prevents the first store of oral care material contained within the first dispenser 250 from accidentally dispensing, leaking, or drying out. In certain embodiments the first dispenser cap 290 may be hingedly coupled to the first dispenser body 251, although the invention is not to be so limited and in other embodiments the first dispenser cap 290 may be completely removable and separable from the first dispenser body 251. Furthermore, in certain embodiments the dispenser caps 290 may be formed as a part of the toothbrush cap 240. Furthermore, in some embodiments the first dispenser cap 290 may be omitted from the oral care system 200.

The second dispenser 350 comprises a second dispenser cap 390 coupled to the second dispenser body 351 of the second dispenser 350. Specifically, the second dispenser cap 390 is coupled to the second dispenser body 351 such as by a tight fit, an interference fit, a threaded screw, fasteners or the like. The second dispenser cap 390 covers the second applicator 352 and the second dispensing orifice 356 when coupled to the second dispenser body 351. Thus, the second dispenser cap 390 prevents the second store of oral care material contained within the second dispenser 350 from accidentally dispensing, leaking, or drying out. In certain embodiments the second dispenser cap 390 may be hingedly coupled to the second dispenser body 351, although the invention is not to be so limited and in other embodiments the second dispenser cap 390 may be completely removable and separable from the second dispenser body 351. Furthermore, in some embodiments the second dispenser cap 390 may be omitted from the oral care system 200.

When the first dispenser 250 is in the first extended state as illustrated in FIG. 6 and the first dispenser cap 290 is removed from the first dispenser body 251, a distal portion 257 of the first dispenser 250 protrudes from the toothbrush body 210 and through the opening 220 in the proximal end 213 of the toothbrush body 210. In the first extended state, the first locking element 270 is nested within the first stop notch 273 as has been described above so that the first dispenser 250 can not be separated from the toothbrush body 210.

The distal portion 257 of the first dispenser 250 includes the first applicator 252 and the first dispensing orifice 256. Thus, when the first dispenser 250 is in the first extended state, a user can cause the first dispenser 250 to dispense the first store of oral care material (or a portion thereof) through the first dispensing orifice 256 to apply the first store of oral care material to his or her teeth and/or other oral surfaces. Dispensing of the first store of oral care material from the first dispenser 250 can be achieved in any of the manners discussed above with regard to the dispenser 150 or by any other techniques.

Although not illustrated, when the second dispenser 350 is in the first extended state and the second dispenser cap 390 is removed from the second dispenser body 351, a distal portion 357 of the second dispenser 350 protrudes from the toothbrush body 210 and through the opening 220 in the proximal end 213 of the toothbrush body 210. In the second extended state, the second locking element 370 is nested within the second stop notch 373 as has been described above so that the second dispenser 350 can not be separated from the toothbrush body 210. The distal portion 357 of the second dispenser 350 includes the second applicator 352 and the second dispensing orifice 356. Thus, when the second dispenser 350 is in the second extended state, a user can cause the second dispenser 350 to dispense the second store of oral care material (or a portion thereof) through the second dispensing orifice 356 to apply the second store of the oral care material to his or her teeth and/or other oral surfaces. Dispensing of the second store of oral care material from the second dispenser 350 can be achieved using any of the techniques discussed herein above.

The oral care materials contained within the dispenser 150 of the oral care system 100 and the first and second dispensers 250, 350 of the oral care system 200 may be a measured amount of a semi-viscous, yet flowable, aesthetically pleasing, pleasant tasting oral care composition that is dosed or metered through the dispensing orifice and delivered directly into a user's oral cavity or onto the tooth cleaning elements. The oral care material can either be a flowable liquid and/or a solid that is easily dispensed for consumer use. The flowable liquids may include, without limitation, pastes, gels, rinses, foams, scrubbers, solids, liquids and/or aerosols under compressed air.

The oral care materials can be used for a variety of oral care needs including but not limited to whitening, sensitivity, gum health, stain-removal, enamel strengthening, mouthrinse, breath spray, sanitizer solution for a toothbrush, and whole mouth care solutions. The oral care material may also include active ingredients typical of use in whole mouth oral care formulations. The oral care material may also contain sweeteners, particulate, and sensates capable of delivering unique benefits to the consumer.

The oral care material can be used as a stand-alone formulation. In some embodiments, the composition has the capability and potential of containing and delivering active ingredients, such as Fluoride, Arginine, Triclosan, or the like, while further providing potential cleaning, stain-removal, whitening of the teeth surface with the incorporation of chemical agents such as hydrogen peroxide, or polishing abrasives such as, for example, silica, dicalcium phosphate, precipitated calcium carbonate or the like. The composition also has the capability of delivering consumer perceivable visual signals via unique colorants, shapes, stripes, sparkles, extruded forms, etc, while further delivering consumer perceivable sensory signals delivered via unique flavors, sweeteners, sensates, or the like.

The oral care materials include materials that provide oral health benefits to a user upon contact with a user's oral cavity. In one embodiment, the oral care materials are fluidic materials. For example, in certain embodiments the oral care materials include a mouthwash solution that cleans the oral surfaces when applied thereto and provides the user with breath freshening benefits. In other embodiments, the oral care materials include a tooth cleaning solution, such as a dentifrice. Of course, the oral care materials are not to be in any way limiting of the present invention and may include fluids having active or inactive agents that deliver therapeutic, cosmetic, experiential and/or sensorial benefits to a consumer during a tooth, soft tissue, tongue or interdental cleaning regimen. Specifically, the oral care material can be an anti-sensitivity agent, fluoride, a tartar protection agent, an antibacterial agent, an oxidative or whitening agent, an enamel strengthening or repair agent, a tooth erosion preventing agent, a gum health active, a nutritional ingredient, a tartar control or anti-stain ingredient, an enzyme, a sensate ingredient, a flavor or flavor ingredient, a breath freshening ingredient, an oral malodor reducing agent, an anti-attachment agent or sealant, a diagnostic solution, an occluding agent, a dry mouth relief ingredient, a catalyst to enhance the activity of any of these agents, colorants or aesthetic ingredients, arginine bicarbonate, chlorohexidine, triclosan, CPC, zinc oxide and combinations thereof. As noted above, in certain embodiments the oral care materials or at least one of the oral care materials is free of a dentifrice as the oral care fluid is intended to supplement traditional brushing of the teeth rather than supplant it.

The formulation or oral care material in the dispensers can be used as a standalone formulation or if using a device with more than one dispenser, the formulations in the applicators can be used in a non-sequential or separate but sequential manner. For example, the non-sequential dispensers could be that one dispenser contains sanitizer spray for the toothbrush while the other contains plaque finding ingredients. In this case, the plaque finding ingredient would be used before brushing and the sanitizer spray in the other applicator would be used after brushing. The two dispensers could also be used in conjunction with one another. In this example, the whitening ingredient in one dispenser may need a sealant to be added in order to work over time. The first dispenser containing the whitening ingredient would then be applied first and the sealant in the second dispenser applied immediately afterward. These two formulas/benefits would not be compatible and/or would not be as effective if used in a single formulation.

It should be appreciated that various combinations of the components and functionality described above with respect to the different embodiments are contemplated within the scope of the present invention. Therefore, certain features of one embodiment can be incorporated into another embodiment. Furthermore, certain features are not described in detail with regard to some of the embodiments with an understanding that the description of that similar feature in the other embodiments is equally applicable. Moreover, although the embodiments are described herein with a single dispenser or with two dispensers, other embodiments are contemplated that use more than two dispensers. In one such embodiment, four dispensers are incorporated.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care system comprising:
   a toothbrush body comprising a handle and a head;
   a plurality of tooth cleaning elements extending from the head;
   an opening in the toothbrush body that forms a passageway into an internal cavity of the handle;
   a first dispenser positioned within the internal cavity and comprising a first store of oral care material, the first dispenser resiliently coupled to the toothbrush body to be alterable between: (1) a first retracted state; and (2) a first extended state, in which a distal portion of the first dispenser protrudes from the opening, and in which a user can apply the oral care material contained within the first dispenser;
   a resiliently-structured first locking element for locking the first dispenser in the first retracted state, the first locking element comprising a first end fixedly attached to the first dispenser and a second end defining a locking portion engaging a corresponding locking depression formed in the handle;
   a first actuator operably coupled to the first locking element;
   wherein when the first dispenser is in the first retracted state and the first actuator is actuated, the first locking element is released from the locking depression and the first dispenser is automatically biased into the first extended state.

2. The oral care system according to claim 1 further comprising a first resilient element comprising a first portion fixed to the toothbrush body and a second portion fixed to the first dispenser.

3. The oral care system according to claim 1 wherein the first dispenser is biased into the first extended state.

4. The oral care system according to claim 1 wherein, when the first dispenser is in the first retracted state, an entirety of the first dispenser is located within the internal cavity; and wherein the distal portion of the first dispenser comprises a first dispensing orifice through which the first store of oral care material can be dispensed.

5. The oral care system according to claim 4 wherein the distal portion of the first dispenser further comprises a first dispenser cap coupled to a first dispenser body of the first dispenser to be alterable between: (1) a closed state in which the first dispenser cap covers the first dispensing orifice; and (2) an open state in which the first dispensing orifice is exposed.

6. The oral care system according to claim 4 further comprising a toothbrush cap coupled to the toothbrush body so as to be alterable between: (1) a closed state in which the toothbrush cap covers the opening; and (2) an open state in which the opening is exposed.

7. The oral care system according to claim 1 wherein the first locking element is alterable between: (1) an outward locked state engaging the locking depression; and (2) an inward released state disengaging the locking depression; and wherein the first locking element is biased into the locked state and actuation of the actuator forces the locking element into the released state.

8. The oral care system according to claim 1 wherein the first dispenser translates between the first retracted state and the first extended state.

9. The oral care system according to claim 1 further comprising a first stopper element that prevents over-extension of the first dispenser beyond the first extended state.

10. The oral care system according to claim 1 wherein a distal portion of the first dispenser comprises a first dispensing orifice and a first dispenser cap coupled to a body of the dispenser, and wherein when the first dispenser is in the retracted state, the first dispenser cap abuts the proximal end of the toothbrush body and covers the opening.

11. The oral care system according to claim 10 wherein the handle of the toothbrush body comprises an outer surface and the first dispenser cap comprises an outer surface, and wherein when the first dispenser is in the retracted state, the outer surfaces of the handle and first dispenser cap form a smooth continuous surface at an interface between the first dispenser cap and the handle.

12. An oral care system comprising:
a toothbrush body comprising a handle and a head;
a plurality of tooth cleaning elements extending from the head;
an opening in the toothbrush body that forms a passageway into an internal cavity of the handle;
a first dispenser positioned within the internal cavity and comprising a first store of oral care material, the first dispenser resiliently coupled to the toothbrush body to be alterable between: (1) a first retracted state; and (2) a first extended state, in which a distal portion of the first dispenser protrudes from the opening, and in which a user can apply the oral care material contained within the first dispenser; and
a first retaining element that prevents the first dispenser from being completely detached from the toothbrush body.

13. An oral care system comprising:
a toothbrush body comprising a handle and a head;
a plurality of tooth cleaning elements extending from the head;
an opening in the toothbrush body that forms a passageway into an internal cavity of the handle;
a first dispenser positioned within the internal cavity and comprising a first store of oral care material, the first dispenser resiliently coupled to the toothbrush body to be alterable between: (1) a first retracted state; and (2) a first extended state, in which a distal portion of the first dispenser protrudes from the opening, and in which a user can apply the oral care material contained within the first dispenser; and
a second dispenser positioned within the internal cavity and comprising a second store of oral care material that is different than the first store of oral care material, the second dispenser resiliently coupled to the toothbrush body to be alterable between: (1) a second retracted state; and (2) a second extended state.

* * * * *